US006632226B2

(12) United States Patent
Chan

(10) Patent No.: US 6,632,226 B2
(45) Date of Patent: *Oct. 14, 2003

(54) APPARATUS AND METHOD FOR DETERMINING THE RELATIVE POSITION OF BONES DURING SURGERY

(76) Inventor: Kwan-Ho Chan, 4803 1st Pl., Lubbock, TX (US) 79410

( * ) Notice: Subject to any disclaimer, the term of this patent is extended or adjusted under 35 U.S.C. 154(b) by 0 days.

This patent is subject to a terminal disclaimer.

(21) Appl. No.: 09/794,950

(22) Filed: Feb. 27, 2001

(65) Prior Publication Data

US 2002/0010474 A1 Jan. 24, 2002

Related U.S. Application Data

(63) Continuation of application No. 09/200,127, filed on Nov. 25, 1998, now Pat. No. 6,193,724.

(51) Int. Cl.[7] .............................................. A61B 17/56
(52) U.S. Cl. ...................................................... 606/102
(58) Field of Search ............................. 606/53, 86–89, 606/100, 102, 67

(56) References Cited

U.S. PATENT DOCUMENTS

| | | | | | |
|---|---|---|---|---|---|
| 4,893,619 | A | * | 1/1990 | Dale et al. | 606/87 |
| 5,074,865 | A | * | 12/1991 | Fahmy | 606/54 |
| 5,122,145 | A | * | 6/1992 | Fishbane | 606/102 |
| 5,235,754 | A | * | 8/1993 | Sirois | 33/27 |
| 5,354,300 | A | * | 10/1994 | Goble et al. | 606/80 |
| 5,423,828 | A | * | 6/1995 | Benson | 606/102 |
| 5,435,321 | A | * | 7/1995 | McMillen et al. | 128/782 |
| 5,603,717 | A | * | 2/1997 | Benson | 606/102 |
| 5,613,971 | A | * | 3/1997 | Lower et al. | 606/96 |
| 5,616,147 | A | * | 4/1997 | Gadelius | 606/102 |
| 5,628,750 | A | * | 5/1997 | Whitlock et al. | 606/88 |
| 5,700,268 | A | * | 12/1997 | Bertin | 606/102 |
| 5,755,794 | A | * | 5/1998 | Benson | 623/16 |
| 5,788,705 | A | * | 8/1998 | Huddleston et al. | 606/102 |
| 6,027,507 | A | * | 2/2000 | Anderson et al. | 606/87 |
| 6,193,724 | B1 | * | 2/2001 | Chan | 606/102 |

* cited by examiner

Primary Examiner—Kevin Shaver
Assistant Examiner—Michael B. Priddy
(74) Attorney, Agent, or Firm—Pandiscio & Pandiscio, P.C.

(57) ABSTRACT

A measuring gauge for measuring the relative position of two bones during surgery, the measuring gauge comprising an anchor, an adapter, an outrigger and a locking joint.

4 Claims, 15 Drawing Sheets

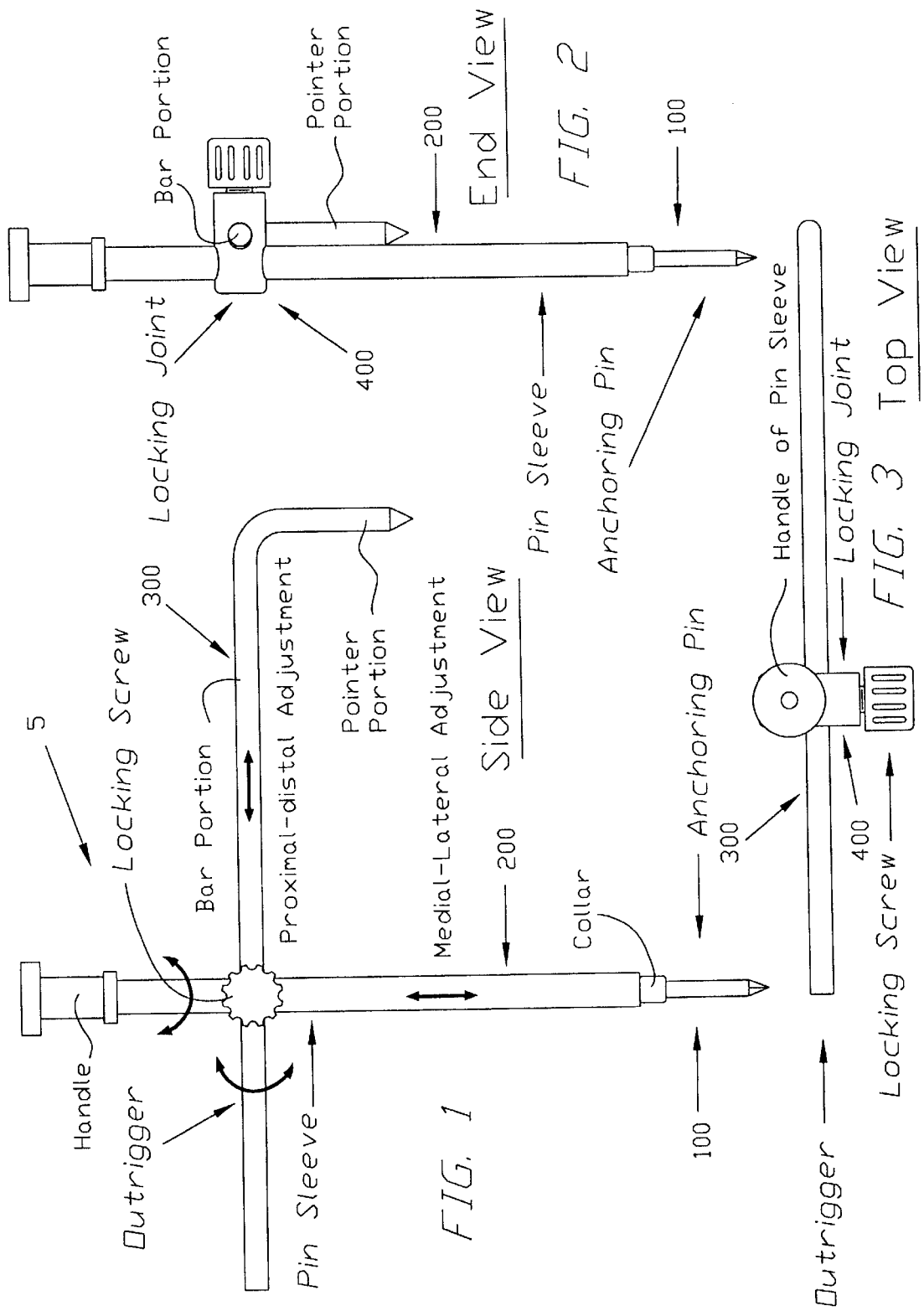

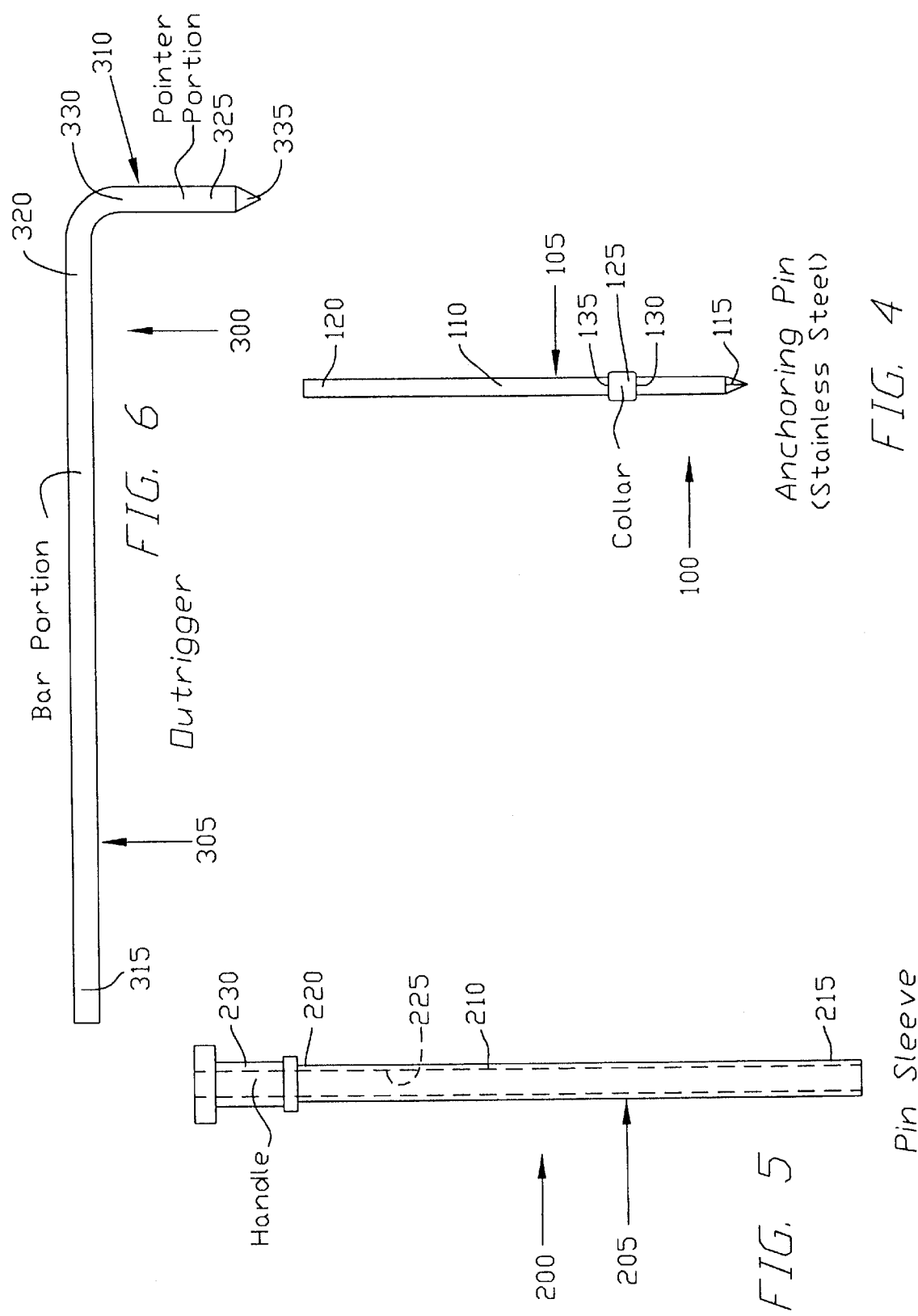

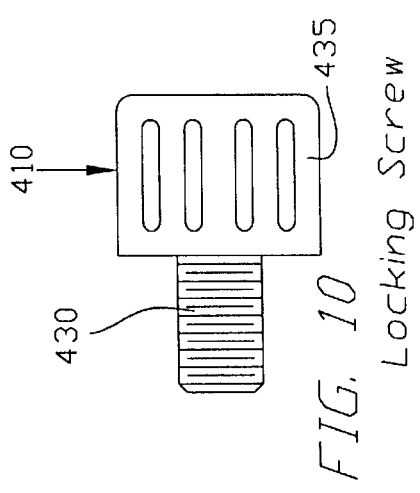
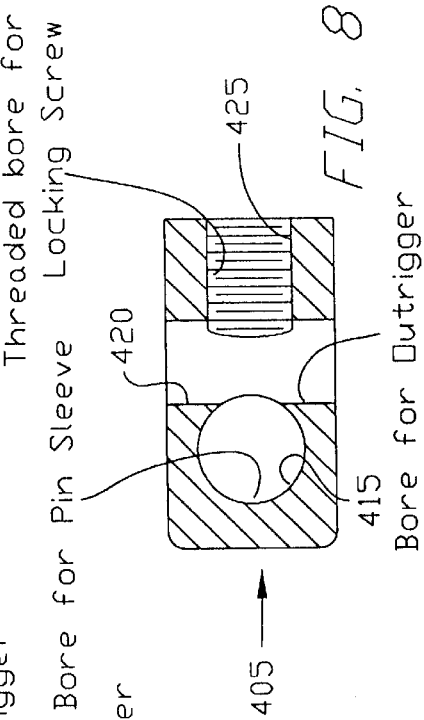
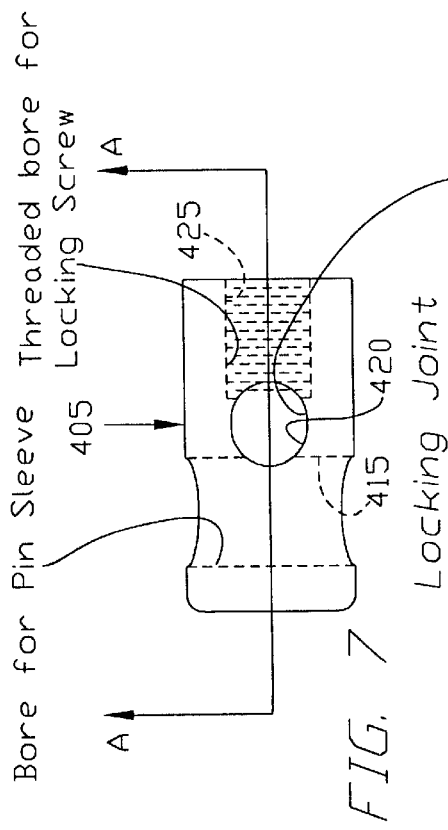
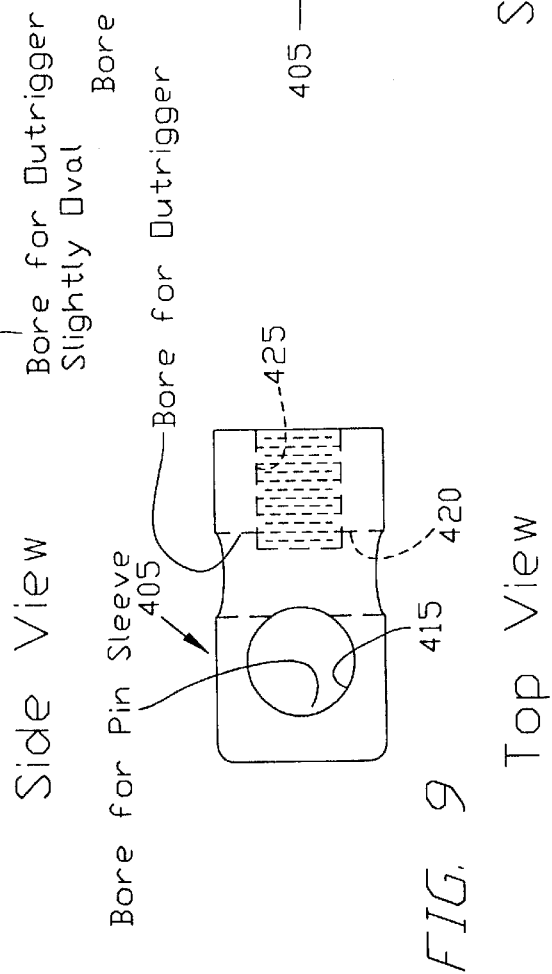

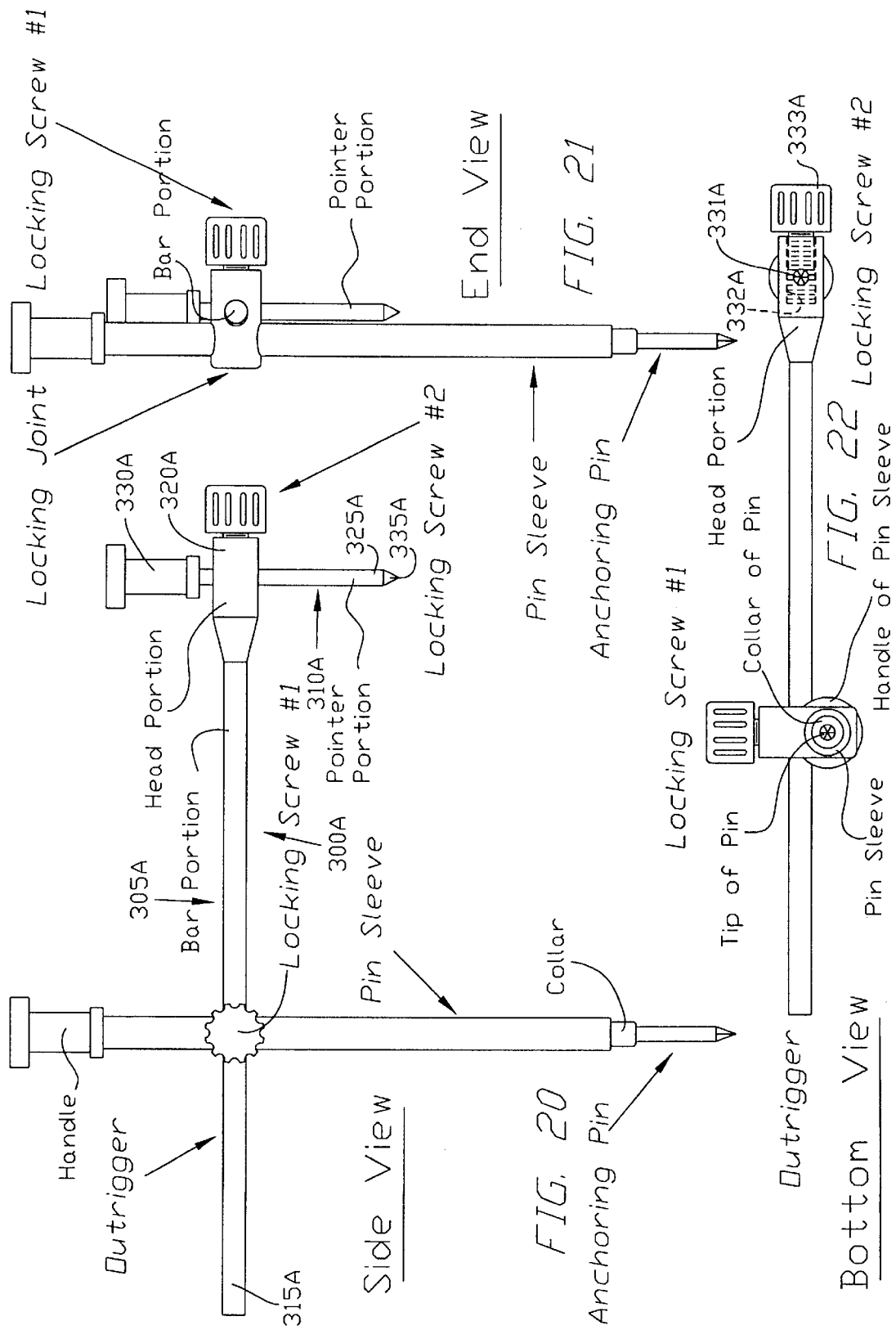

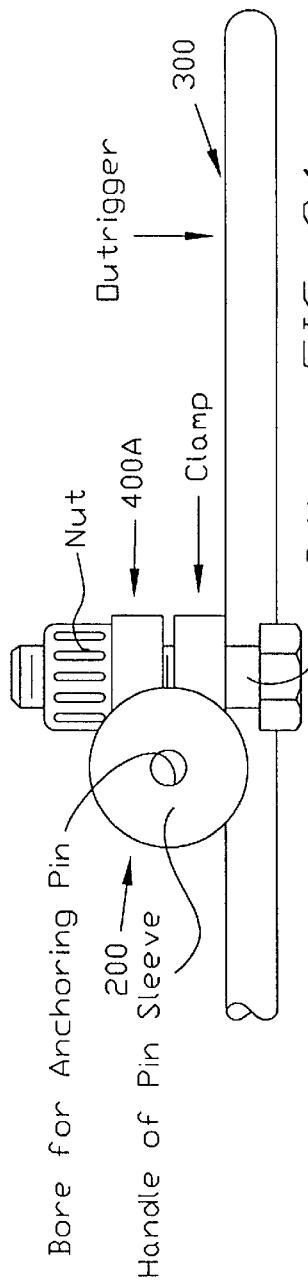
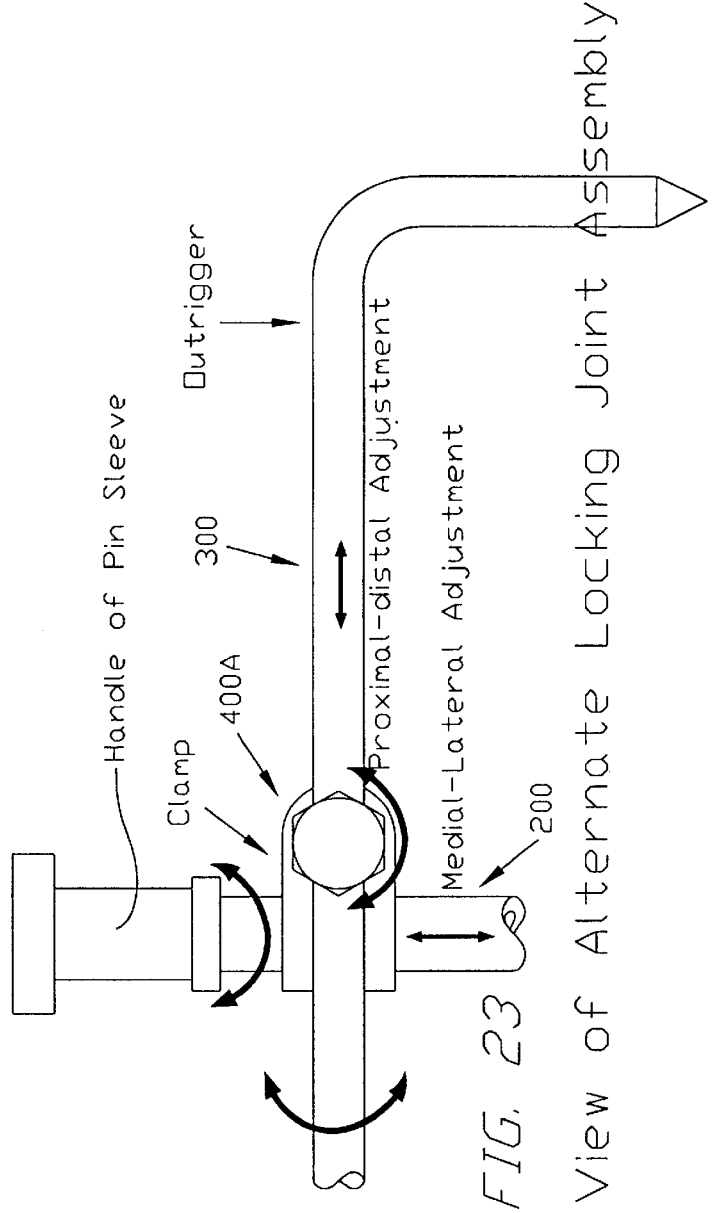
FIG. 24
Top View of Alternate Locking Joint Assembly
FIG. 23
Side View of Alternate Locking Joint Assembly

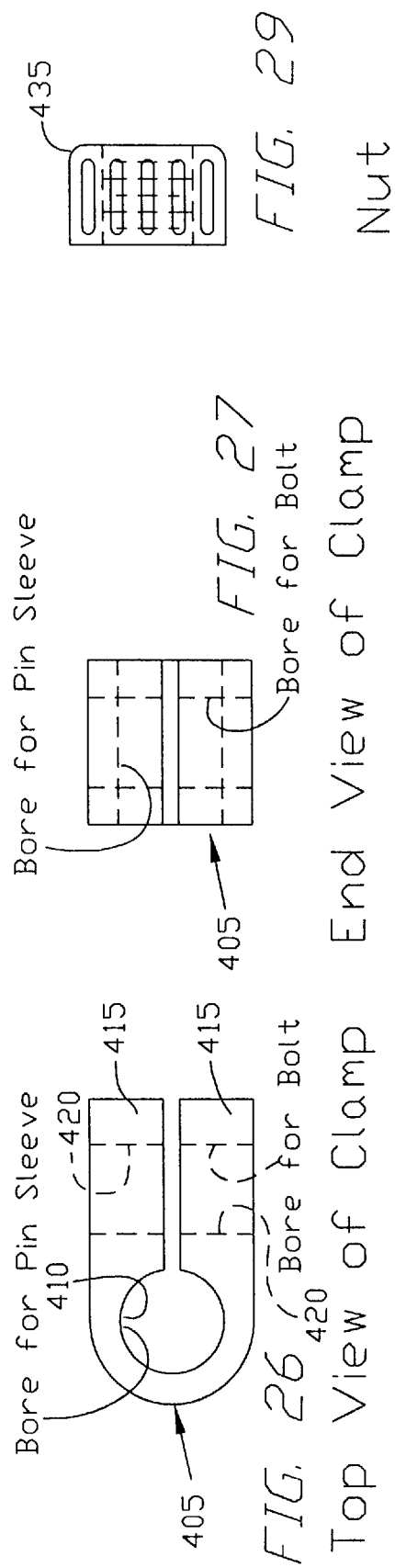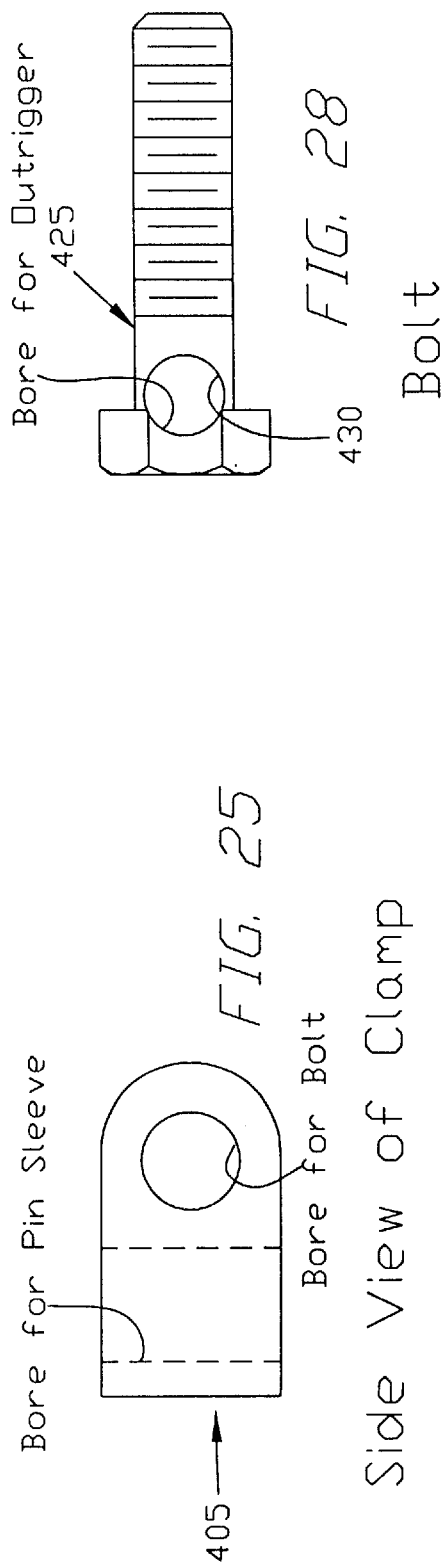

APPARATUS AND METHOD FOR DETERMINING THE RELATIVE POSITION OF BONES DURING SURGERY

REFERENCE TO PENDING PRIOR PATENT APPLICATION

This is a continuation of prior U.S. Pat. No. 6,193,724 application Ser. No. 09/200,127, filed Nov. 25, 1998 is now by Kwan-Ho Chan for APPARATUS AND METHOD FOR DETERMINING THE RELATIVE POSITION OF BONES DURING SURGERY.

FIELD OF THE INVENTION

This invention relates to surgical apparatus and procedures in general, and more particularly to surgical apparatus and procedures for determining the relative position of bones during surgery, and still more particularly to surgical apparatus and procedures for determining the distal displacement and lateral offset of a patient's femur relative to that patient's ilium during total hip replacement surgery.

BACKGROUND OF THE INVENTION

Unacceptable leg length inequalities, mis-sized lateral offsets, and joint dislocations are possible adverse outcomes of total hip replacement surgeries. Leg length inequalities and mis-sized lateral offsets (including, particularly, insufficient lateral offsets) can result in a persistent limp for patients who have undergone total hip replacement surgeries. Also, joint dislocations are more likely to occur if the soft tissue tension across the replaced joint is too lax as a result of a shortened limb and/or an insufficient lateral offset.

It is, therefore, generally desirable to maintain the leg length, and the amount of lateral offset, which existed prior to the total hip replacement surgery. Sometimes, however, it may he desirable during total hip replacement surgery to change the leg length, and/or the amount of lateral offset, so as to compensate for deficiencies existing in the hip joint prior to the total hip replacement surgery.

The desired leg length, and the desired lateral offset, are achieved during the total hip replacement surgery by selecting a femoral head prosthesis which has the appropriate neck length and geometry, and/or by varying the amount of bone resection performed on the femur.

To achieve the desired leg length and lateral offset during total hip replacement surgery, the surgeon typically determines the initial (i.e., pre-dislocation) position of the femur relative to the ilium, based on reference points selected on each of these bones. A number of different devices and methods for measuring the position of the femur relative to the ilium are known in the art. These existing devices and methods are generally used in conjunction with one or more reference pins which are inserted into a convenient location in the ilium, e.g., typically a few centimeters above the acetabulum. The position of the patient's femur is then measured off the aforementioned one or more reference pins, by measuring to an appropriate reference point on the femur, e.g., typically in the area of the greater trochanter. It should be appreciated that the femoral reference point is typically located in the area of the greater trochanter inasmuch as the greater trochanter is not removed during femoral resection, yet is on the upper part of the femur and hence reasonably close to the patient's ilium so as to facilitate measurement.

By way of example, various devices and methods for measuring the position of the femur relative to the ilium are disclosed in U.S. Pat. Nos. 5,122,145; 5,423,828; 5,435,321; 5,603,717; 5,616,147; 5,700,268; and 5,755,794.

Unfortunately, however, all of the existing devices and methods for measuring the position of the femur relative to the ilium tend to suffer from one or more significant disadvantages. On the one hand, some of the existing devices only measure the longitudinal displacement of the femur, and they do not measure the lateral offset of the femur. On the other hand, in those devices which can measure both the longitudinal displacement and lateral offset of the femur, the devices tend to be relatively bulky and complicated to install and use.

OBJECTS OF THE INVENTION

Accordingly, one object of the present invention is to provide an improved apparatus for simultaneously determining the distal displacement and lateral offset of the femur relative to the ilium.

Another object of the present invention is to provide an apparatus for simultaneously determining the distal displacement and lateral offset of the femur relative to the ilium, wherein the apparatus is adapted for easy installation and removal, whereby a major portion of the apparatus can be temporarily removed from the surgical site so as to provide unobstructed access to the surgical site.

And another object of the present invention is to provide an apparatus for simultaneously determining the distal displacement and lateral offset of the femur relative to the ileum, wherein the apparatus is safe and effective for use in total hip replacement surgeries.

Still another object of the present invention is to provide an apparatus for determining the distal displacement and lateral offset of the femur relative to the ileum, wherein the apparatus will reduce the amount of time normally required to determine the distal displacement and lateral offset of the femur relative to the ileum.

Yet another object of the present invention is to provide an apparatus for determining the relative position of bones during surgery, wherein the bones may comprise bones other than the femur and the ileum.

And another object of the present invention is to provide an improved method for measuring the distal displacement and lateral offset of the femur relative to the ilium.

And another object of the present invention is to provide an improved method for determining the relative position of bones during surgery.

SUMMARY OF THE INVENTION

These and other objects of the present invention are addressed by the provision and use of a novel measuring gauge for determining the relative position of bones during surgery.

The novel measuring gauge comprises an anchor, preferably made of stainless steel, having a pointed tip for insertion into, and temporary attachment to, the ilium of the patient. A stop is preferably located on the anchor about 1 to 3 centimeters from the pointed tip. The stop prevents excessive penetration of the anchor into the ilium, which might injure internal organs or neurovascular structures.

An adapter slidingly engages the anchor and sits atop the stop. The pointed tip of the anchor is driven into the ilium bone at a convenient location, usually a few centimeters above the acetabulum. The pointed tip can be driven into the bone by impacting the anchor directly, or by impacting the adapter mounted on the anchor.

An outrigger, comprising a shaft which preferably has a pointer at one end, is adjustably connected to the adapter by a releasable locking joint. The outrigger's pointer preferably projects at a right angle to the longitudinal axis of the outrigger.

In use, after surgical exposure of the hip joint, and prior to the dislocation of the joint for bone resection, a reference mark, preferably one to two millimeters deep, is made at a convenient location on the greater trochanter of the femur using a sharp pointed device such as the tip of a pin. Alternatively, the reference mark can be made with a marking pen or an electrocautery device. The anchor (with or without the adapter mounted thereon) is positioned in the ilium as described above.

Next, the elements of the measuring gauge are arranged so that the outrigger is adjustably connected to the adapter by the releasable locking joint, with the adapter being seated on the anchor. The tip of the pointer can then be positioned in three dimensional space, using the following degrees of freedom of the adapter, locking joint and outrigger: (1) the locking joint, together with the outrigger, is slidable along the longitudinal axis of the adapter; (2) the locking joint and outrigger can also rotate about the longitudinal axis of the adapter and/or about the longitudinal axis of the anchor; (3) the shaft of the outrigger can also telescope in and out of the locking joint; and (4) the outrigger can also rotate around the long axis of its shaft.

Using the aforementioned degrees of freedom, the measuring gauge is manipulated so that the outrigger's pointer is positioned over the reference mark on the femur. At this stage, the adapter and outrigger are securely locked together, in a fixed relative position, by firmly tightening the locking joint. In this manner, the position of the reference mark on the femur, relative to the anchor installed on the ilium, is clearly established vis-à-vis the elements of the measuring gauge.

Thereafter, the adapter, locking joint and outrigger are slidingly disengaged from the anchor, as a locked unit, so as to provide the surgeon with unobstructed access to the hip joint.

The hip joint is then dislocated for resection of the appropriate amount of femoral bone.

Following initial preparation of the bone bed, a trial prosthesis is installed in the patient's femur. This initial trial prosthesis is selected by the surgeon, from an assortment of different prostheses, according to the surgeon's initial estimate of which prosthesis will achieve the desired results.

The hip joint is then reduced so that the surgeon can check for proper alignment of the prosthesis, any leg length discrepancy, proper lateral offset, and the stability of the hip joint from dislocation. More particularly, after the hip joint has been reduced, the surgeon repositions the adapter, locking joint and outrigger, as a locked unit, over the anchor. This permits the surgeon to check for proper distal displacement and lateral offset of the femur relative to the ilium, by observing any displacement of the outrigger's pointer from the reference mark placed on the femur's greater trochanter.

In the usual case, i.e., where the original geometry of the patient's joint was correct and is to be maintained during the total hip replacement surgery, an appropriate prosthesis will be selected so as to ensure that the outrigger's pointer is substantially aligned with the reference mark placed on the femur's greater trochanter.

In other cases, however, the geometry of the patient's joint is to be changed during the total hip replacement surgery, by varying the distal displacement and/or lateral offset of the femur relative to the ilium. In this case, the desired joint correction is achieved by selecting an appropriate femoral prosthesis so as to ensure that the outrigger's pointer is displaced a desired distance from the reference mark placed on the femur's greater trochanter.

After the surgeon has noted the position of the outrigger's pointer relative to the reference mark placed on the femur's greater trochanter, the adapter, locking joint and outrigger are then removed, again as a locked unit.

The joint is then dislocated once more, the trial prosthesis is removed, and the permanent prosthesis installed. As noted above, the desired amount of distal displacement and lateral offset is achieved by carefully choosing a prosthesis component of the proper size and geometry, and/or by varying, where possible, the amount of bone which is resected.

After the trial prosthesis has been replaced by the permanent prosthesis, the joint is reduced, and a final check of the joint can be made with the measuring gauge.

Prior to wound closure, the measuring gauge, including the anchor fastened to the ilium, is removed from the surgical site.

BRIEF DESCRIPTION OF THE DRAWINGS

These and other objects and features of the present invention will be more fully disclosed or rendered obvious by the following detailed description of the preferred embodiment of the invention, which is to be considered together with the accompanying drawings wherein like numbers refer to like parts and further wherein:

FIG. 1 is a side view of a measuring gauge formed in accordance with the present invention;

FIG. 2 is an end view of the measuring gauge shown in FIG. 1;

FIG. 3 is a top view of the measuring gauge shown in FIG. 1;

FIG. 4 is a side view of the measuring gauge's anchor;

FIG. 5 is a side view of the measuring gauge's adapter;

FIG. 6 is a side view of the measuring gauge's outrigger;

FIGS. 7–9 shown details of the locking joint's housing;

FIG. 10 shows details of the locking joint's locking screw;

FIGS. 20–22 show an alternative form of the measuring gauge; and

FIGS. 23–29 show another alternative form of the measuring gauge.

DETAILED DESCRIPTION OF THE PREFERRED EMBODIMENT

Figure 11:
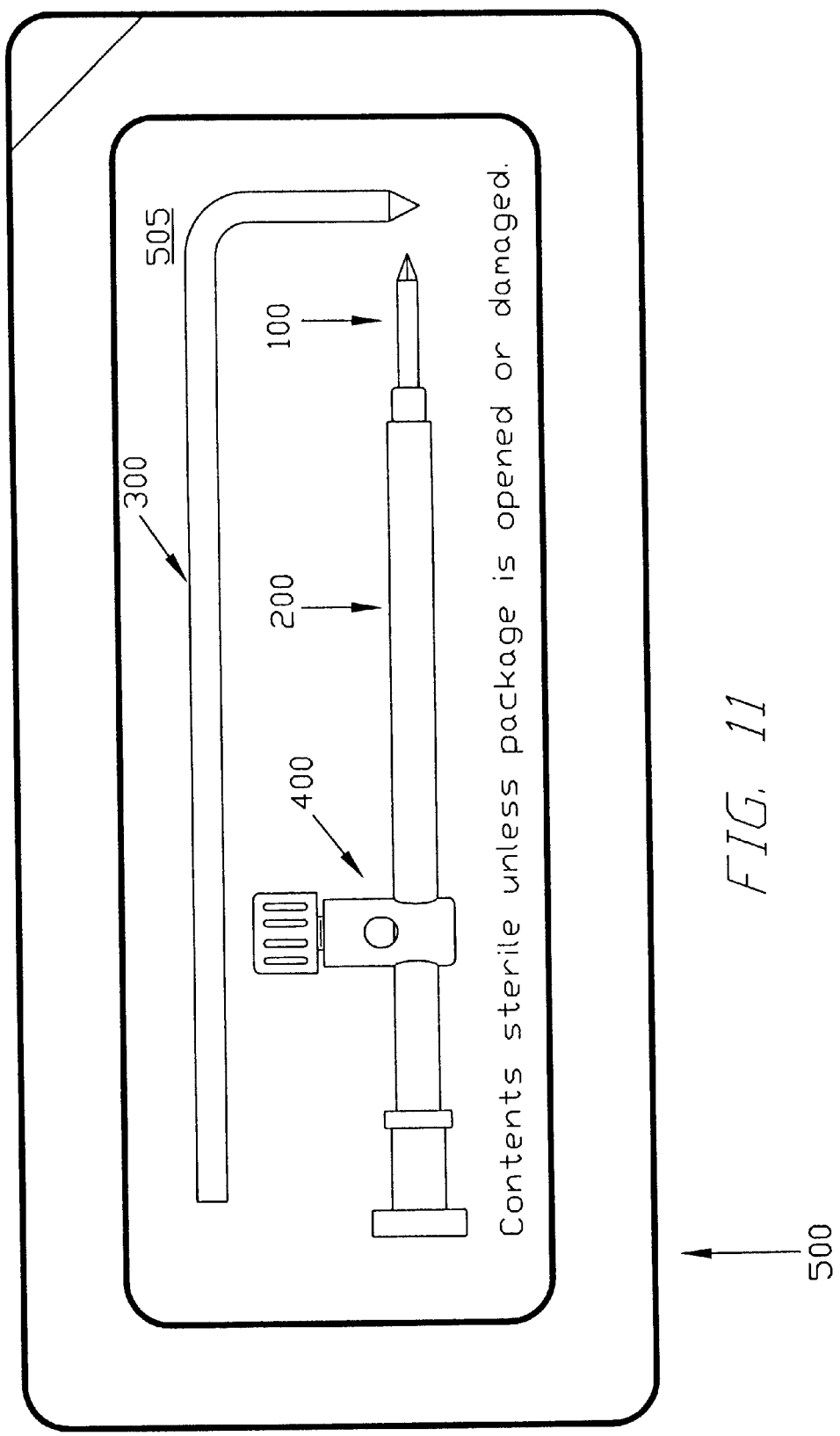
FIG. 11 is a top plan view of a measuring gauge kit formed in accordance with the present invention.

Looking first at FIGS. 1–3, there is shown a measuring gauge 5 which generally comprises an anchor 100, an adapter 200, an outrigger 300 and a locking joint 400.

Looking next at FIGS. 1–3 and 4, anchor 100 preferably comprises an anchoring pin 105. Anchoring pin 105 generally comprises a body 110 having a pointed distal end 115, a proximal end 120, and a diametrically-enlarged collar 125. Collar 125 terminates in a distal end surface, or first shoulder, 130 and a proximal end surface, or second shoulder, 135.

Looking next at FIGS. 1–3 and 5, adapter 200 preferably comprises a pin sleeve 205. Pin sleeve 205 generally comprises a body 210 having a distal end 215, a proximal end 220, and an interior bore 225 opening on distal end 215 and extending at least part of the way, and preferably all of the way, to proximal end 220. The internal diameter of interior bore 225 is such that there is a frictional fit between pin sleeve 205 and body 110 of anchoring pin 105. Preferably a handle 230 is attached to proximal end 220 of pin sleeve 205.

Looking next at FIGS. 1–3 and 6, outrigger 300 preferably comprises a bar portion 305 and a pointer portion 310. More particularly, bar portion 305 comprises a first end 315 and a second end 320, and pointer portion 310 comprises a first end 325 and a second end 330. The second end 320 of bar portion 305 is connected to the second end 330 of pointer portion 310 so that the two elements together form a generally L-shaped element. The first end 325 of pointer portion 310 preferably terminates in a point so as to constitute a pointer 335.

Looking next at FIGS. 1–3 and 7–10, locking joint 400 preferably comprises a housing 405 and a locking screw 410.

Housing 405 has three bores formed therein: a first bore 415 extending completely through housing 405, a second bore 420 also extending completely through housing 405, and a third bore 425 extending at least partially through housing 405. More particularly, first bore 415, second bore 420 and third bore 425 extend at right angles to one another, with first bore 415 and second bore 420 intersecting one another intermediate their respective lengths, and with third bore 425 intersecting second bore 420 at the interior end of third bore 425. Third bore 425 is threaded.

Locking screw 410 comprises a threaded shaft 430 and a head 435. The locking screw's shaft 430 is threaded, and is sized, so as to be received in the housing's third bore 425.

In practice, and as will hereinafter be discussed in further detail, it is intended that adapter 200, outrigger 300 and locking joint 400 may all be assembled into an adjustable subassembly unit, which subassembly unit may itself be mounted on, or dismounted from, anchor 100.

More particularly, it is intended that the aforementioned adjustable subassembly unit be formed by extending the pin sleeve's distal end 215 through the locking joint's first bore 415, and by passing the first end 315 of the outrigger's bar portion 305 through the locking joint's second bore 420, such that (1) when the locking screw's threaded shaft 430 is advanced an appropriate distance into the locking joint's third bore 425, pin sleeve 205, outrigger 300 and locking joint 400 will constitute a substantially rigid subassembly, and (2) when the locking screw's threaded shaft 430 is withdrawn an appropriate distance out of the locking joint's third bore 425, pin sleeve 205, outrigger 300 and locking joint 400 may be adjustably positioned relative to one another.

Looking next at FIG. 11, measuring gauge 5 is intended to have its constituent components (i.e., anchor 100, adapter 200, outrigger 300 and locking joint 400) packaged in a tray 500. Preferably tray 500 is filled with the measuring gauge components at the time of manufacture, and then the tray is sealed with a transparent top tear sheet 505 so as to form a pre-packaged kit which may thereafter be opened at the time of use. As is well known in the art, tray 500 and its constituent components may be sterilized either before or after the tray is sealed with top tear sheet 505.

In one preferred form of the invention, anchor 100, adapter 200 and locking joint 400 are pre-assembled together within tray 500, in the manner shown in FIG. 11, before the tray is sealed with top tear sheet 505. In this position, the distal end 215 of pin sleeve 215 will engage and rest on the proximal end surface 135 of the anchoring pin's collar 125.

Hip gauge 5 is intended to be used as follows.

Figure 12:
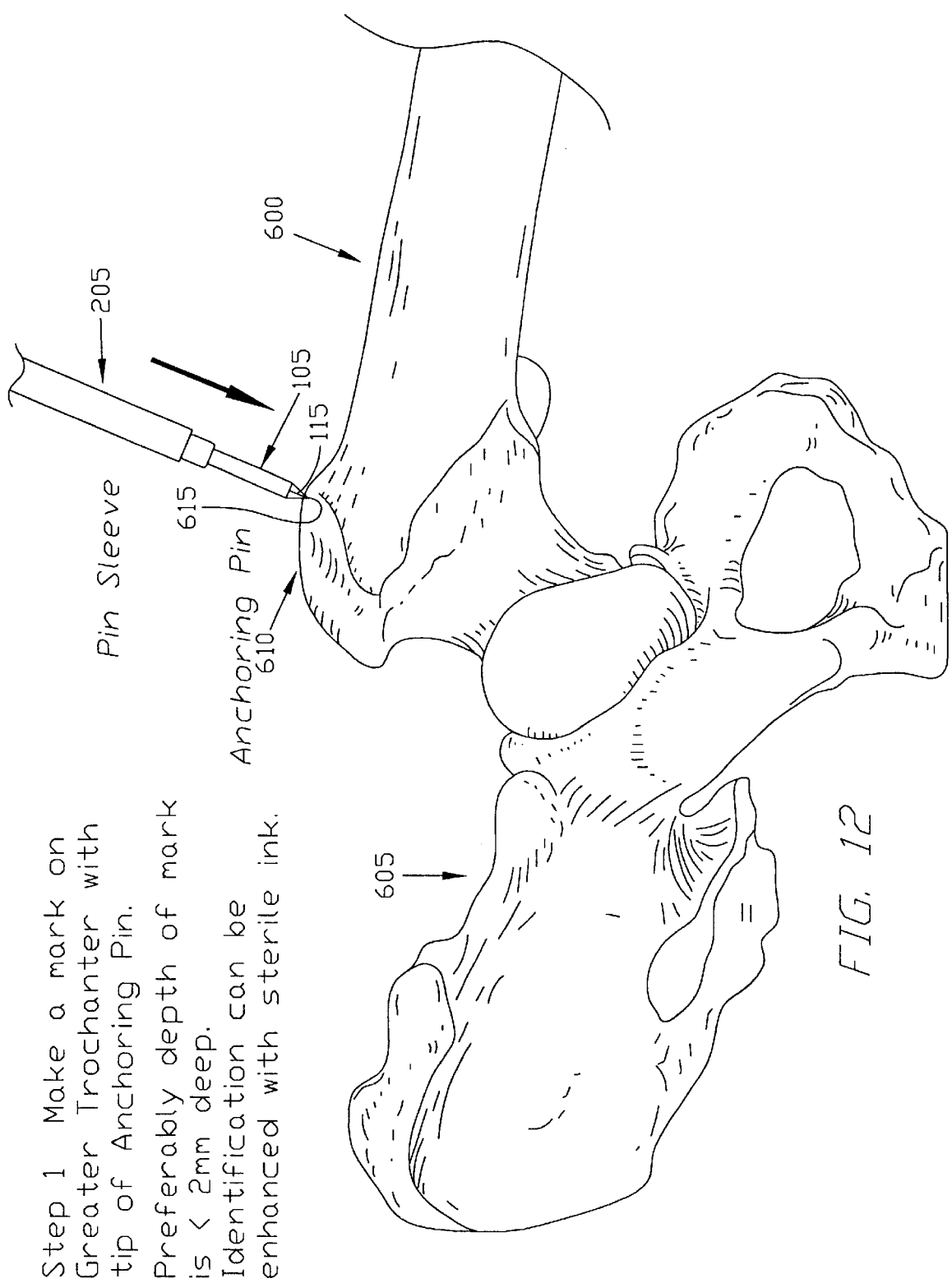
FIGS. 12–19 are schematic views showing how the measuring gauge may be used in a total hip replacement procedure.

Initially, the hip joint is surgically exposed in the traditional manner, so as to present the surgeon with access to the patient's femur 600 and ilium 605 (see FIG. 12). Then a mark 615 (FIG. 12) is made on the femur's greater trochanter 610, preferably using pointed distal end 115 of anchoring pin 105. Preferably the depth of the mark is less than 2 millimeters deep. If desired, this mark can be enhanced with sterile ink. Alternatively, the mark may be placed on greater trochanter 610 using some other device, such as a marking pen or an electrocautery device.

Figure 13:
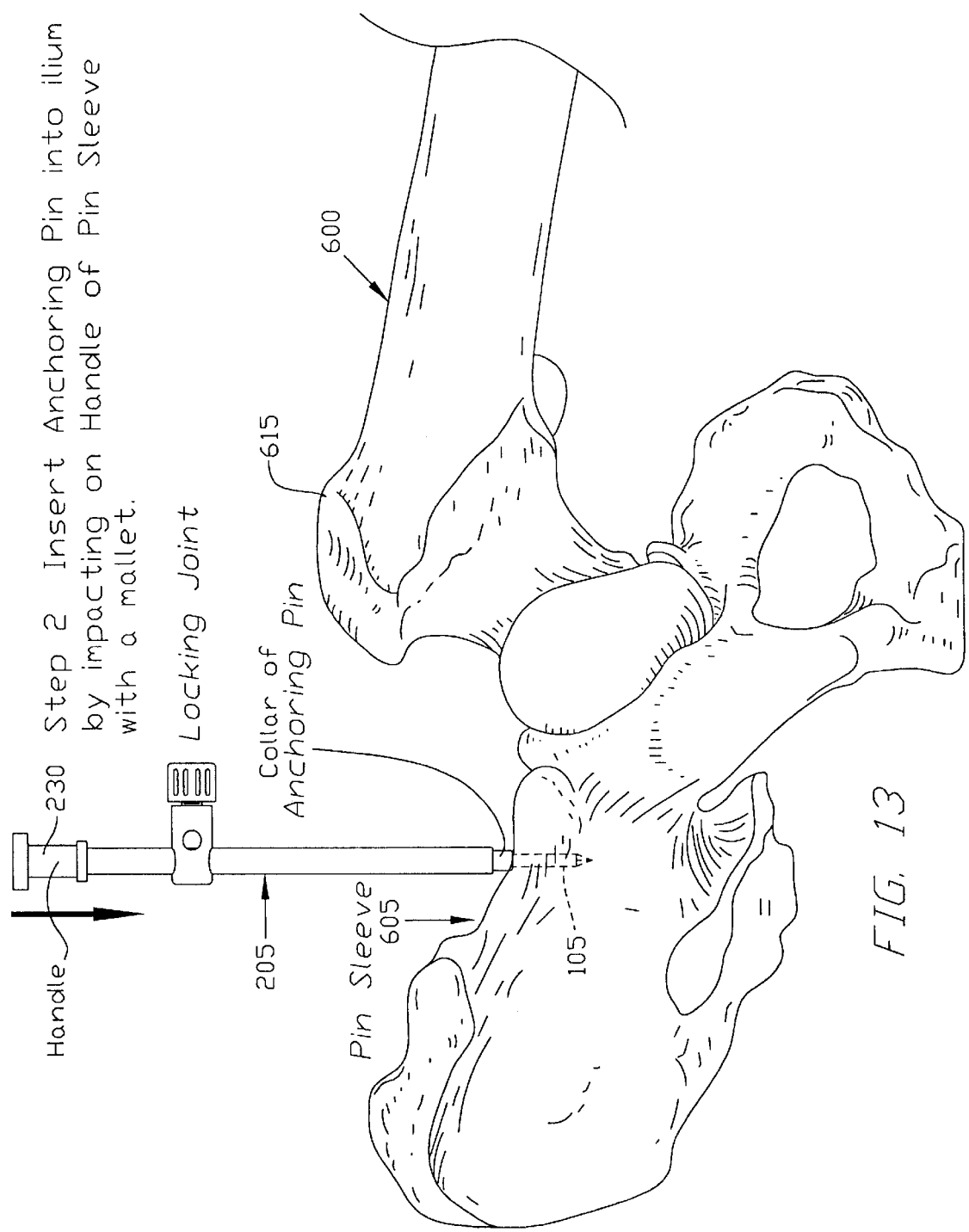

Next, the pointed distal end 115 of anchoring pin 105 is driven into the patient's ilium 605 (see FIG. 13) by impacting on handle 230 of pin sleeve 205 with a mallet. Anchoring pin 105 is driven into the patient's ilium 605 until collar 125 of the anchoring pin engages the outer surface of the ilium, whereupon further penetration of the anchoring pin into the ilium is prohibited. In general, a line extending between the entry point of anchoring pin 105 in ilium 605 and the mark 615 on femur 600, is substantially parallel to the coronal plane of the patient's trunk.

Figure 14:
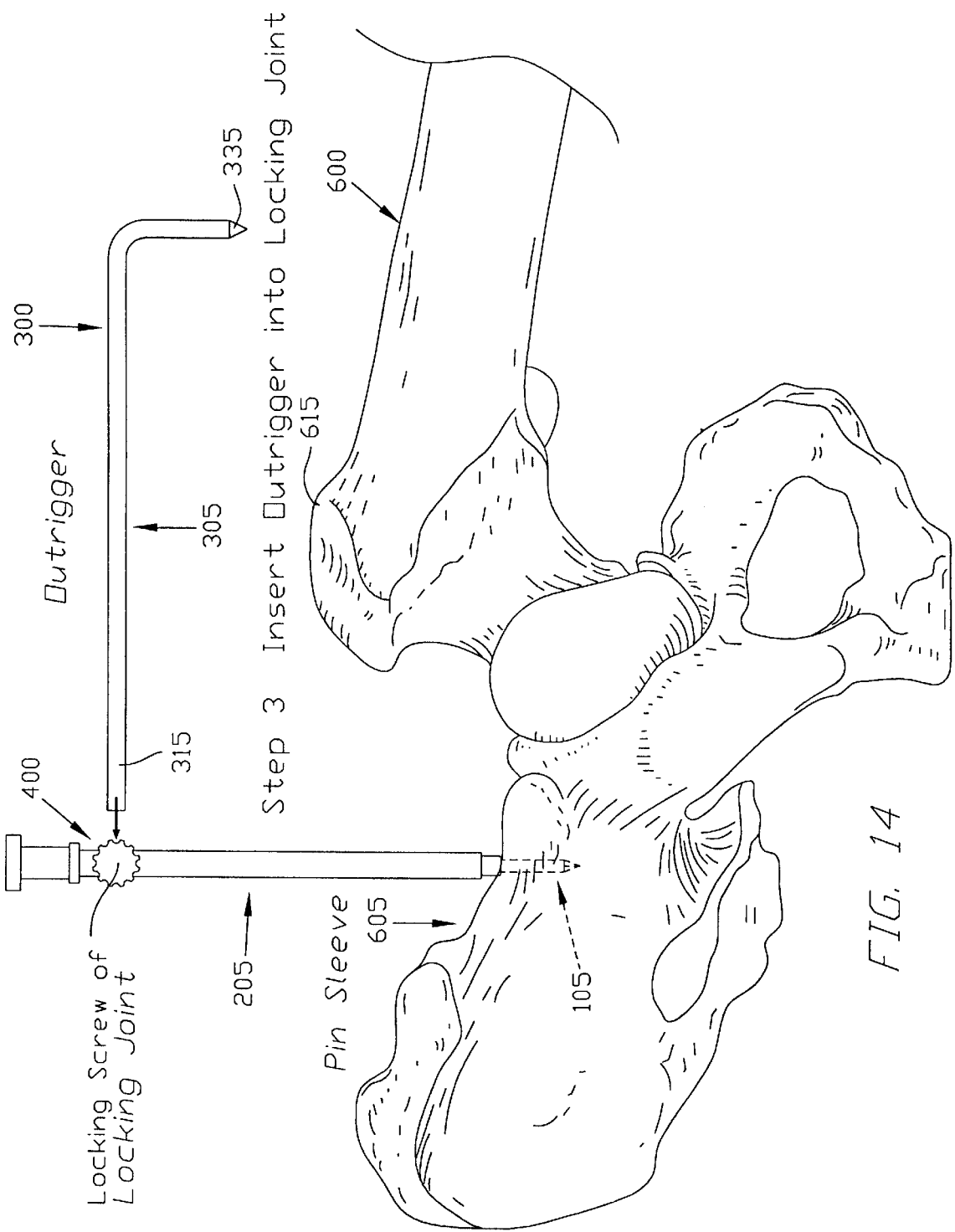

At this point, outrigger 300 is attached to locking joint 400 (see FIG. 14), by passing the first end 315 of the outrigger's bar portion 305 through second bore 420 of the locking joint.

Figure 15:
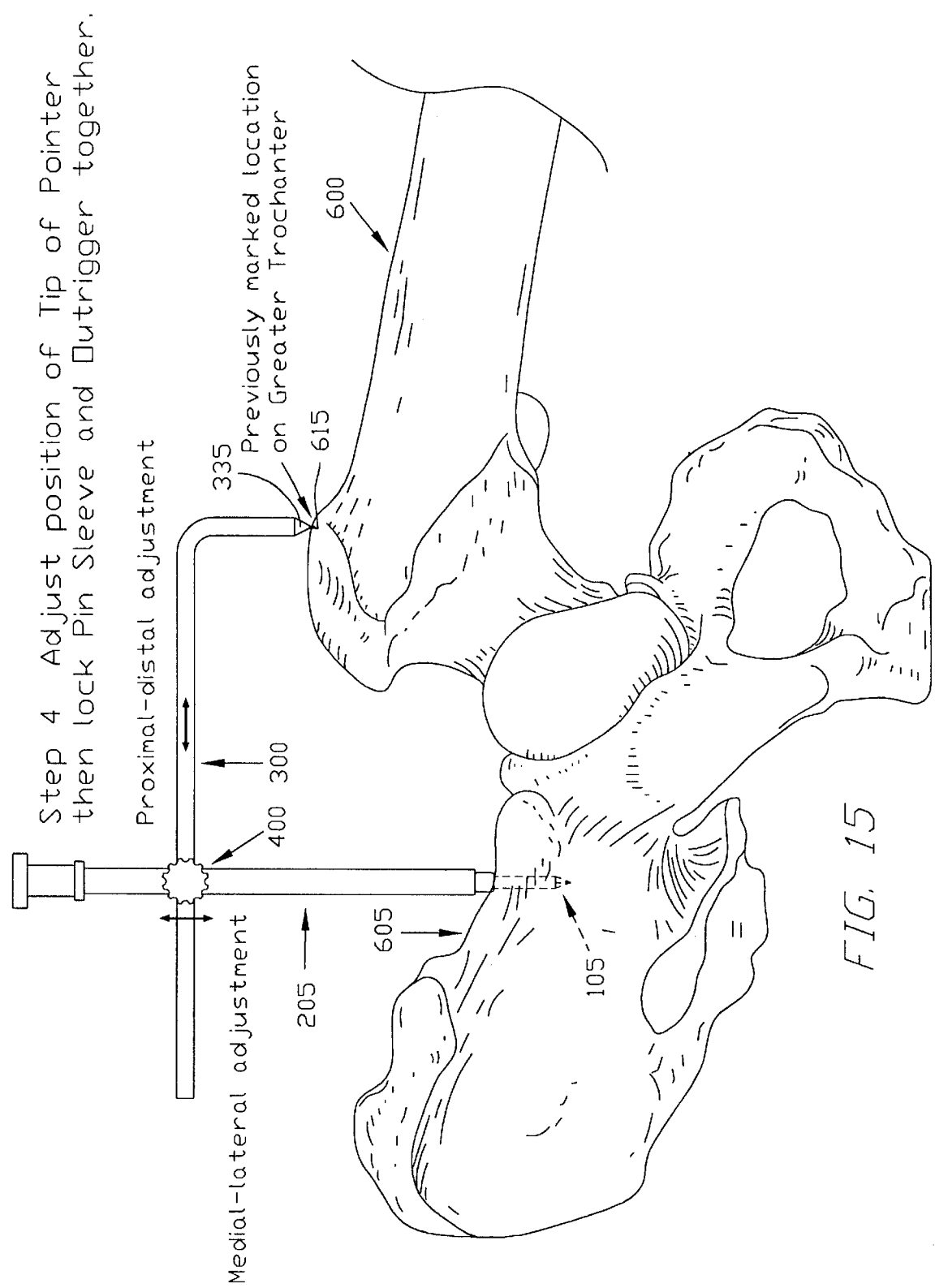

With locking screw 410 loose enough to permit adjustment of pin sleeve 205 and outrigger 300 relative to locking joint 400, measuring gauge 5 is manipulated so that pointer 335 of the outrigger is positioned on the mark 615 previously made on the femur's greater trochanter (see FIG. 15).

Once this has been done, the measuring gauge's locking screw 410 is tightened so as to lock pin sleeve 205 and outrigger 300 in position relative to one another.

Figure 16:
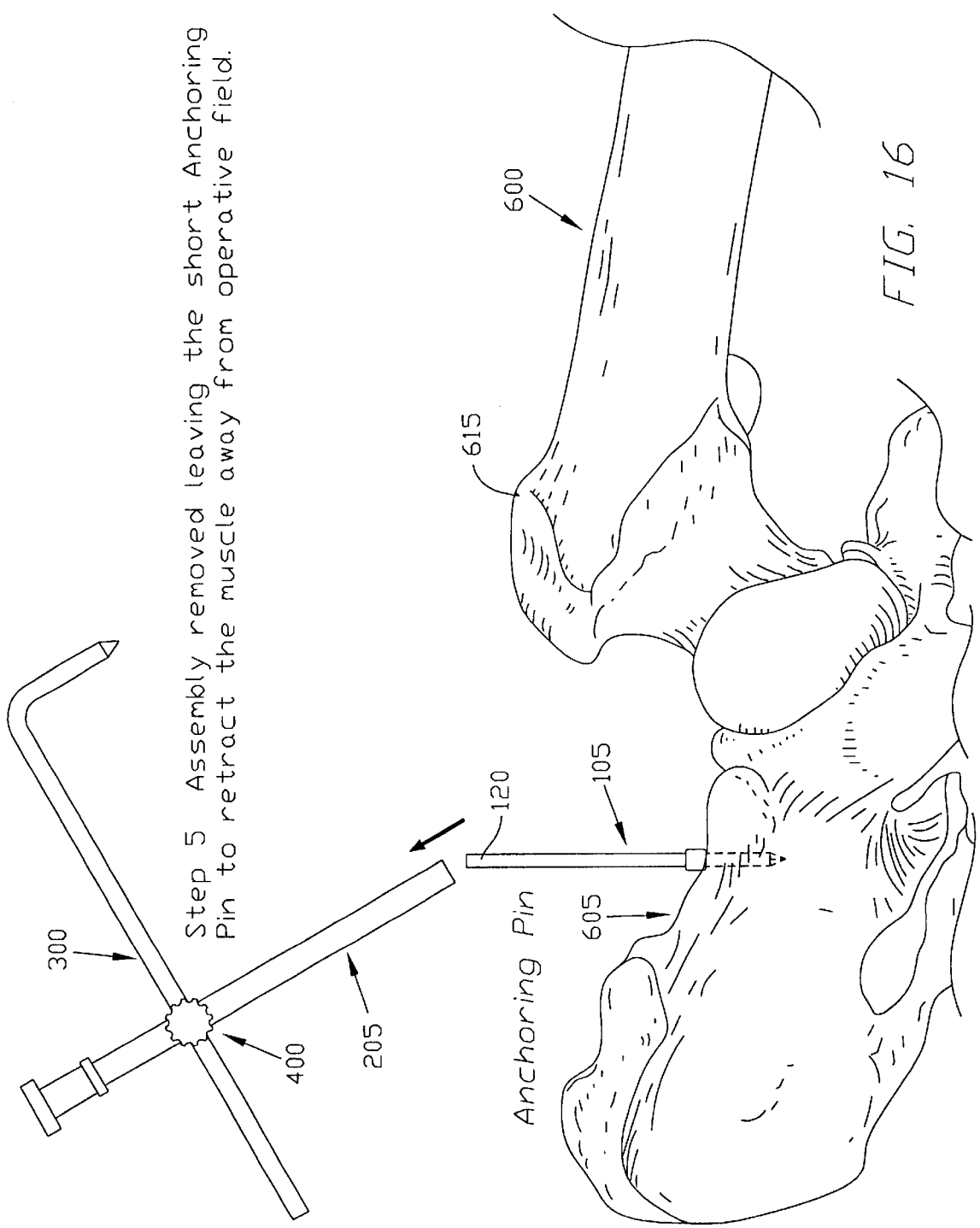

Then, the pin sleeve 205, outrigger 300 and locking joint 400 are removed from anchoring pin 105 as a single locked unit, by withdrawing the pin sleeve off proximal end 120 of anchoring pin 105 (FIG. 16). This leaves anchoring pin 105 secured in the patient's ilium 605 (see FIG. 16), but with the hip joint fully exposed to the surgeon.

At this point, the surgeon proceeds forward with the total hip replacement surgery in the traditional way, i.e., the hip is dislocated, the upper end of the femur is resected, and trial prostheses are installed in the femur and the acetabulum.

Once the trial prostheses have been installed in the patient, the hip joint is reduced, permitting the surgeon to check for proper alignment of the prostheses, any leg length discrepancy, proper lateral offset, and the stability of the hip joint from dislocation. This may be quickly and easily accomplished using the present invention, i.e., by re-installing pin sleeve 205, outrigger 300 and locking screw 400 (which are locked together as a single unit) back onto anchoring pin 105 and then noting the position of the outrigger's pointer 335 relative to the mark 615 previously made on the patient's femur (see FIG. 17). It should be appreciated that when pin sleeve 205, outrigger 300 and locking screw 400 are re-installed as a locked unit back onto anchoring pin 105, care is taken to ensure that the pin sleeve's distal end 215 engages the anchoring pin's collar 125, whereby measuring gauge 5 will occupy exactly the same position it previously occupied relative to the patient's hip joint.

Figure 17:
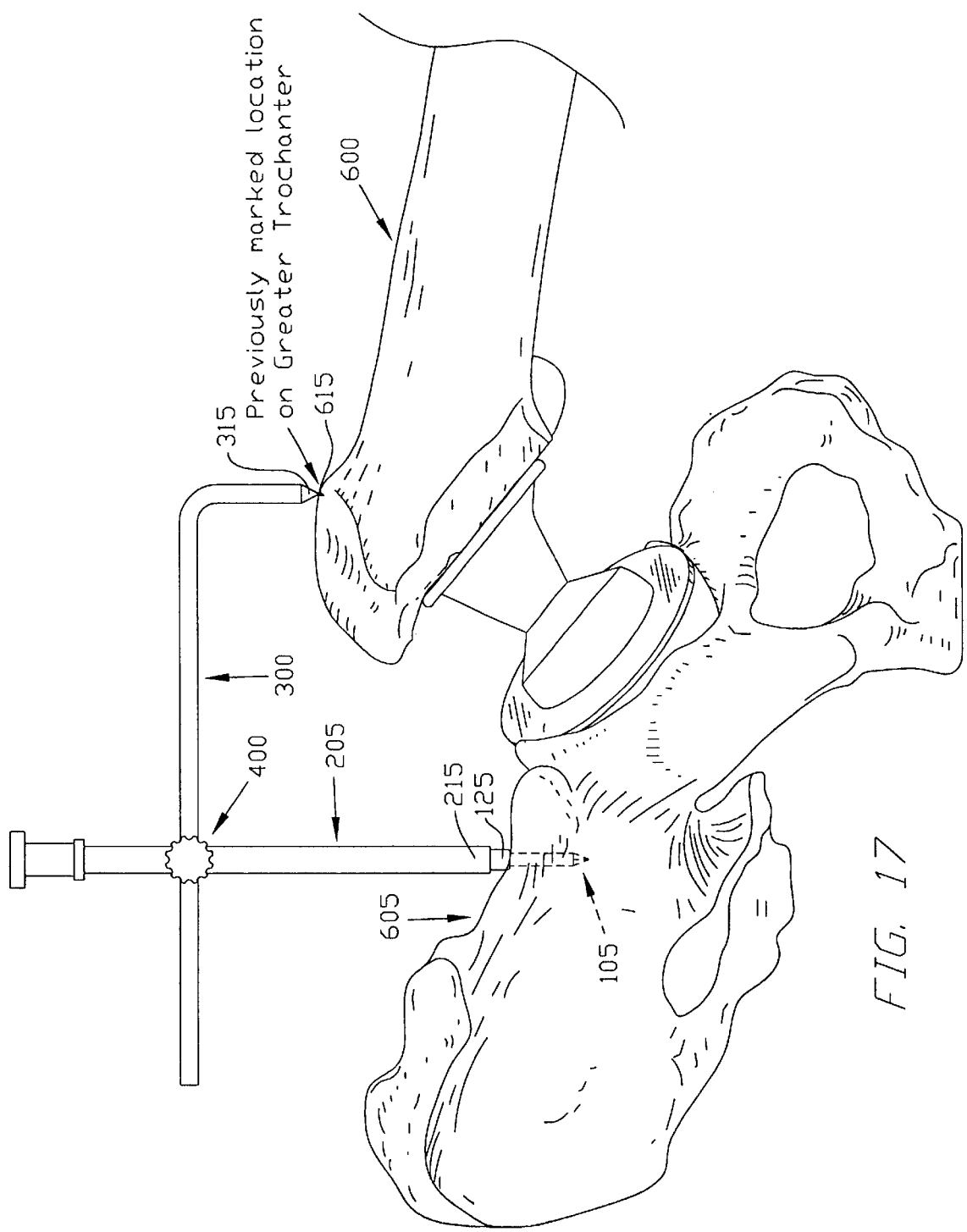

In some cases, the outrigger's pointer 335 may be perfectly aligned with the mark 615 made on the patient's femur (see FIG. 17). In this case, the surgeon will know that the prosthesis is essentially restoring the hip joint to its original condition.

Figure 18:
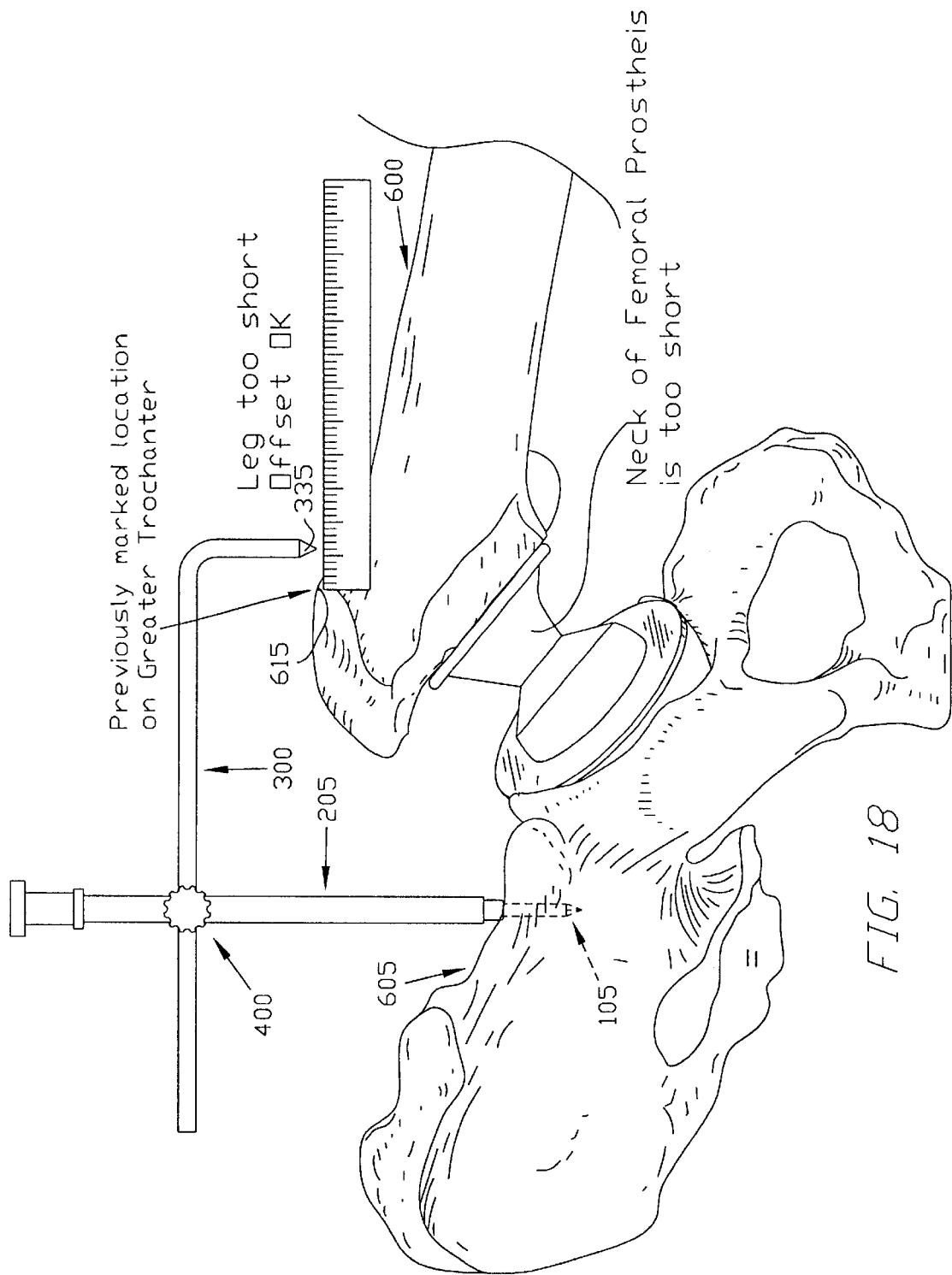

In other cases, the outrigger's pointer 335 may be longitudinally displaced from the mark 615 made on the patient's femur (see FIG. 18). In this case, the surgeon will know that the prosthesis is causing a change in the patient's leg length.

Figure 19:
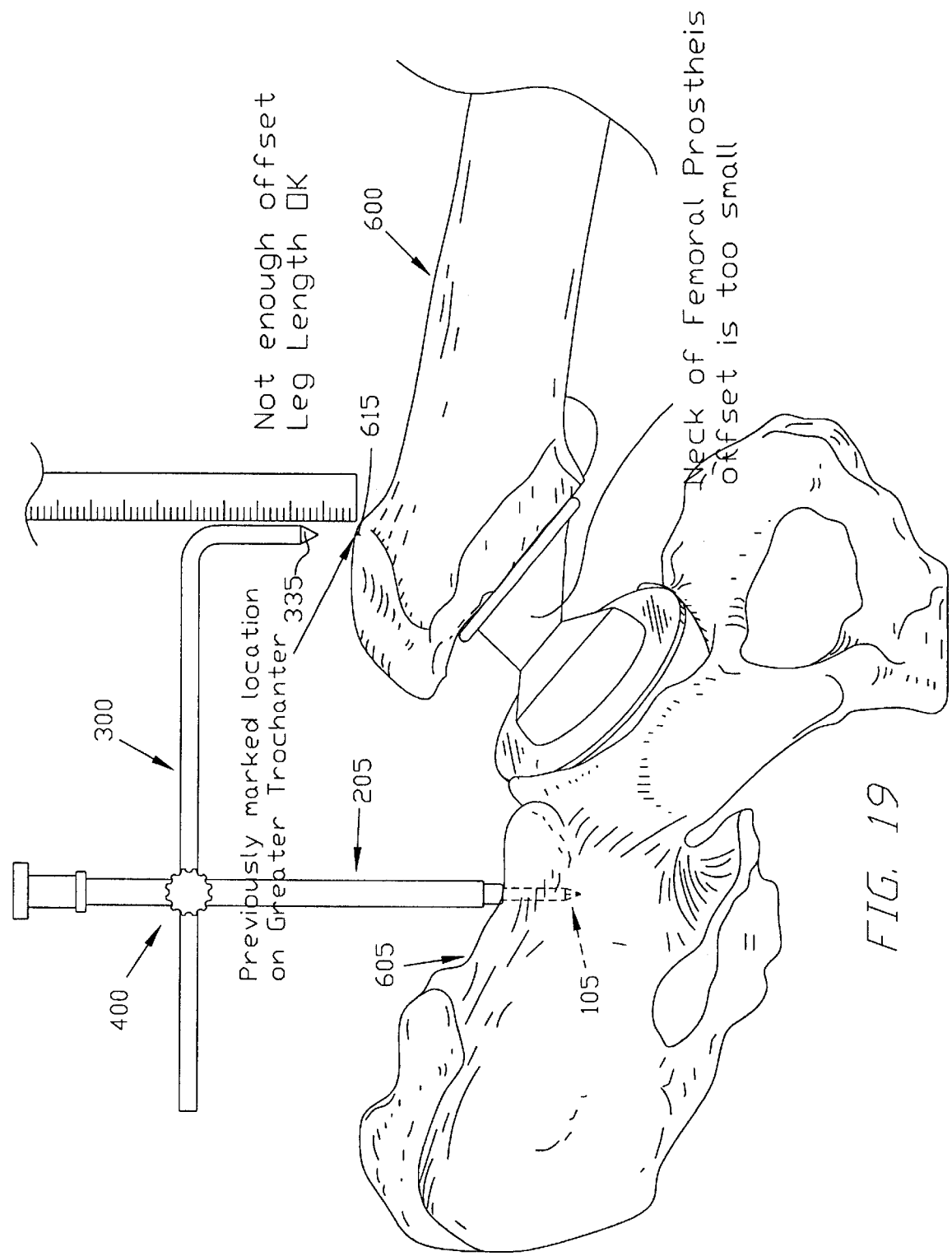

And in other cases, the outrigger's pointer 335 may be laterally displaced from the mark 615 made on the patient's femur (see FIG. 19). In this case, the surgeon will know that the prosthesis is causing a change in the lateral displacement of the patient's leg.

The surgeon can then take any such measurements into account as the operation proceeds forward.

More particularly, pin sleeve 205, outrigger 300 and locking joint 400 are thereafter removed as a locked unit from anchoring pin 105, a permanent prosthesis installed in the patient's femur, and then the joint reduced again. Then measuring gauge 5 may be used to re-check the position of the joint, by re-inserting pin sleeve 205, outrigger 300 and locking screw 400, as a locked unit, over anchoring pin 105. Again, this permits the surgeon to check for proper distal displacement and proper lateral offset, by observing the position of the outrigger's pointer 335 relative to the mark 615 made on the patient's greater trochanter. If the surgeon finds that the position of the outrigger's pointer 335 is not correct relative to the mark 615 made on the patient's greater trochanter, the procedure can be repeated so as to install an alternative prosthesis.

Once the surgeon is satisfied that the proper prosthesis has been selected, pin sleeve 205, outrigger 300 and locking screw 400 is removed, as a locked unit, from anchoring pin 105. Then anchoring pin 105 is removed from the patient's ilium 605, and the total hip replacement surgery proceeds forward in the traditional manner.

MODIFICATIONS OF THE PREFERRED EMBODIMENT

It is, of course, possible to modify the preferred embodiment discussed above without departing from the scope of the present invention.

Thus, for example, outrigger 300 may be replaced by the outrigger 300A shown in FIGS. 20–22. Outrigger 300A comprises a bar portion 305A and a pointer portion 310A. More particularly, bar portion 305A comprises a first end 315A and a second end 320A, and pointer portion 310A comprises a first end 325A and a second end 330A. The second end 320A of bar portion 305A includes a smooth bore 331A (FIG. 22), and a threaded bore 332A (FIG. 22) which intersects bore 331A. Smooth bore 331A is sized to receive pointer portion 310A, and threaded bore 332A is sized to receive a locking screw 333A (FIG. 22), whereby the outrigger's pointer portion 310A may be adjustably positioned relative to the outrigger's bar portion 305A. The first end 325A of pointer portion 310A preferably terminates in a point so as to constitute a pointer 335A.

In use, outrigger 300A is used exactly the same as outrigger 300 disclosed above, except that the position of pointer portion 310A may be adjusted relative to the position of bar portion 305A.

It is also possible to replace the locking joint 400 previously disclosed with an alternative form of locking joint. By way of example but not limitation, it is possible to replace locking joint 400 with the locking joint 400A shown in FIGS. 23–29. Locking joint 400A generally comprises a U-shaped housing 405 (FIG. 26) having a first bore 410 formed therein, and a pair of legs 415. A second bore 420 is formed in legs 415. Locking joint 400A also comprises a bolt 425 (FIG. 28) having a bore 430 formed therein, and a nut 435 (FIG. 29) sized to fit on the threaded end of bolt 425. The housing's first bore 410 is sized to receive the measuring gauge's pin sleeve 205, and the housing's second bore 420 is sized to receive bolt 425. The bolt's bore 430 is sized to receive the bar portion 305 of outrigger 300 (or the bar portion 305A of outrigger 300A). As a result of this construction, by loosening nut 435 on bolt 425, the positions of pin sleeve 205 and outrigger 300 (or outrigger 300A) may be adjusted relative to locking joint 400A and, hence, relative to one another. However, by tightening nut 435 on bolt 425, the relative positions of pin sleeve 205 and outrigger 300 (or outrigger 300A) may be locked relative to locking joint 400A and, hence, relative to one another.

It should also be appreciated that, while in the foregoing description, the present invention has been discussed in the context of a total hip replacement surgery, it is also possible to use the present invention in connection with other joint reconstructions. Thus, for example, the measuring gauge may be used in a total knee replacement surgery, or a total elbow replacement surgery, etc.

It is also possible to use the present invention in surgeries involving bones, but not necessarily involving joints.

In essence, the measuring gauge of the present invention may be used in a wide range of surgeries where the relative position of bones must be determined during such surgery.

ADVANTAGES OF THE INVENTION

Numerous advantages are achieved through the provision and use of the present invention.

For one thing, the present invention provides an improved apparatus for simultaneously determining the distal displacement and lateral offset of the femur relative to the ileum.

And the present invention provides apparatus for simultaneously determining the distal displacement and lateral offset of the femur relative to the ilium, wherein the apparatus is adapted for easy installation and removal, whereby a major portion of the apparatus can be temporarily removed from the surgical site so as to provide unobstructed access to the surgical site.

And the present invention provides apparatus for simultaneously determining the distal displacement and lateral offset of the femur relative to the ilium, wherein the apparatus is safe and effective to use in total hip replacement surgeries.

In addition, the present invention provides apparatus for determining the distal displacement and lateral offset of the femur relative to the ilium, wherein the apparatus will reduce the amount of time normally required to determine the distal displacement and lateral offset of the femur relative to the ilium.

Also, the present invention provides apparatus for determining the relative position of bones during surgery, where the bones comprise bones other than the femur and the ilium.

And the present invention provides an improved method for measuring the distal displacement and lateral offset of the femur relative to the ilium.

Furthermore, the present invention provides an improved method for determining the relative position of bones during surgery.

What is claimed is:

1. A measuring gauge for measuring the relative position of two bones during surgery, the measuring gauge comprising an anchor, an adaptor, an outrigger and a locking joint:

said anchor being adapted for attachment to a first bone of the patient;

said adaptor being adapted for removable attachment to said anchor and comprising a first axis;

said outrigger comprising a pointer and a second axis;

said locking joint having a first bore, a second bore, and a third bore therethrough, said locking joint being adapted for adjustable attachment to said adaptor within said first bore such that said locking joint may be selectively pivoted about and moved along said first axis; and said outrigger is adapted for adjustable attachment to said locking joint such that said outrigger may be selectively pivoted about and moved along said second axis;

whereby when said anchor is attached to the first bone of the patient, said locking joint may be selectively pivoted about and moved along said first axis, and said outrigger may be pivoted about and moved along its second axis, until said pointer is aligned with a reference point located on a second bone of the patient, and then a single locking screw advanced an appropriate distance into said third bore of said locking joint may be adjusted so as to secure said locking joint to said adaptor and so as to secure said outrigger to said locking joint, whereupon said adapter, said locking joint and said outrigger may be removed as a unit from said anchor.

2. A measuring gauge for measuring the relative position of two bones during surgery, the measuring gauge comprising an anchor, an adaptor, an outrigger and a locking joint:

said anchor being adapted for attachment to a first bone of a patient;

said adaptor being adapted for removable attachment to said anchor and comprising a first axis;

said outrigger comprising a pointer and a second axis;

said locking joint having a first bore, a second bore, and a third bore therethrough, said locking joint being adapted for adjustable attachment to said adaptor within said first bore such that said locking joint may be selectively pivoted about and moved along said first axis;

said outrigger is adapted for adjustable attachment to said locking joint such that said outrigger may be selectively pivoted about and moved along said second axis; and said first axis and said second axis extend at a substantially right angle to one another;

whereby when said anchor is attached to the first bone of the patient, said locking joint may be selectively pivoted about and moved along said first axis, and said outrigger may be pivoted about and moved along its second axis, until said pointer is aligned with a reference point located on a second bone of the patient, and then a single locking screw advanced an appropriate distance into said third bore of said locking joint may be adjusted so as to secure said locking joint to said adaptor and so as to secure said outrigger to said locking joint, whereupon said adapter, said locking joint and said outrigger may be removed as a unit from said anchor.

3. A measuring gauge for measuring the relative position of two bones during surgery, said measuring gauge comprising an anchor, an adaptor, an outrigger and a locking joint:

said anchor being adapted for attachment to a first bone of a patient and comprising a pin having a point at one end;

said adaptor being adapted for adjustable attachment to said anchor and comprising a sleeve adapted to be mounted over said pin;

said pin comprising first and second shoulders on said anchor, wherein said second shoulder is spaced from said first shoulder, and further wherein said sleeve is adapted to contact said second shoulder when said adaptor is mounted on said anchor;

said outrigger comprising a pointer;

said locking joint having a first bore, a second bore, and a third bore therethrough, said locking joint being adapted for adjustable attachment to said adaptor within said first bore; and said outrigger being adapted for adjustable attachment to said locking joint within said second bore;

whereby said anchor is attached to the first bone of the patient, said locking joint may be selectively adjusted relative to said adaptor, and said outrigger may be selectively adjusted relative to said locking joint, until said pointer is aligned with a reference point located on a second bone of the patient, and then a single locking screw advanced an appropriate distance into said third bore of said locking joint may be adjusted so as to secure said locking joint to said adaptor and so as to secure said outrigger to said locking joint, whereupon said adaptor, locking joint and outrigger may be removed as a unit from said anchor.

4. A measuring gauge for measuring the relative position of two bones during surgery, said measuring gauge comprising an anchor, an adapter, an outrigger and a locking joint:

said anchor being adapted for attachment to a first bone of a patient;

said adaptor being adapted for removable attachment to said anchor;

said outrigger comprising a pointer and a bar portion, wherein said pointer is adjustably mounted to said bar portion;

said locking joint having a first bore, a second bore, and a third bore therethrough, said locking joint being adapted for adjustable attachment to said adaptor within said first bore; and said outrigger being adapted for adjustable attachment to said locking joint within said second bore;

whereby when said anchor is attached to the first bone of the patient, said locking joint may be selectively adjusted relative to said adaptor, and said outrigger may be selectively adjusted relative to said locking joint, until said pointer is aligned with a reference point located on a second bone of the patient, and then a single locking screw advanced an appropriate distance into said third bore of said locking joint may be adjusted so as to secure said locking joint to said adaptor and so as to secure said outrigger to said locking joint, whereupon said adaptor, locking joint and outrigger may be removed as a unit from said anchor.

* * * * *